United States Patent [19]

Coker et al.

[11] Patent Number: 4,690,933
[45] Date of Patent: Sep. 1, 1987

[54] PYRIDYLVINYL-1H TETRAZOLE HAVING ANTIHISTAMINE ACTIVITY

[75] Inventors: Geoffrey G. Coker, Bromley, England; John W. A. Findlay, Chapel Hill, N.C.

[73] Assignee: Burroughs Wellcome Co., Research Triangle Park, N.C.

[21] Appl. No.: 635,433

[22] Filed: Jul. 27, 1984

[51] Int. Cl.$^4$ .................. C07D 401/02; A61K 31/44
[52] U.S. Cl. ..................... 514/343; 546/276; 546/281; 546/192; 546/194; 546/333; 546/21; 546/22; 548/578; 548/254; 544/124; 564/15; 564/316; 514/340; 514/318; 514/357; 514/89
[58] Field of Search ............ 546/281, 276, 194, 333, 546/21, 22; 544/124; 514/340, 343, 318, 357, 89

[56] References Cited

U.S. PATENT DOCUMENTS

| | | | |
|---|---|---|---|
| 2,567,245 | 5/1948 | Sperber et al. | 546/333 |
| 2,712,020 | 6/1955 | Adamson | 546/281 |
| 2,712,023 | 6/1955 | Adamson | 546/281 |
| 2,991,289 | 7/1961 | Schulte | 546/281 |
| 4,501,893 | 2/1985 | Findlay et al. | 546/281 |

FOREIGN PATENT DOCUMENTS 807757 1/1959 United Kingdom .

Primary Examiner—Jane T. Fan
Attorney, Agent, or Firm—Donald Brown

[57] ABSTRACT

The invention provides compounds of the formula (I)

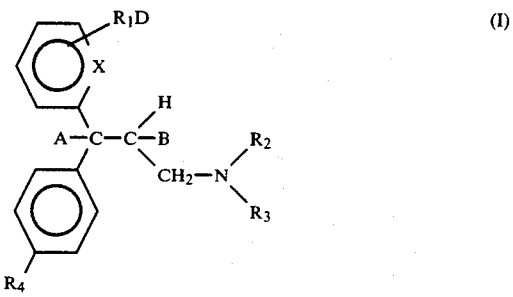

or salts, esters, or amides or other protected forms thereof; wherein $R_1$ is a $C_{1-7}$ bivalent aliphatic hydrocarbon group or a single bond;

$R_2$ and $R_3$ are the same or different and are each hydrogen, $C_{1-4}$ alkyl or taken together with the nitrogen comprise a nitrogen-containing heterocyclic ring having four to six ring members;

X is $-N=$ or $-CH=$;

A and B each represent hydrogen atoms or $-CA-CB-$ represents $-C=C-$; and D is an acidic group other than a carboxylic acid group.

Also provided are pharmaceutical compositions of compounds of the formula (I), methods for the preparation of the compounds and intermediates in their preparation.

The compounds of the formula (I) have antihistamic activity.

3 Claims, No Drawings

PYRIDYLVINYL-1H TETRAZOLE HAVING ANTIHISTAMINE ACTIVITY

The present invention relates to new chemical compounds exhibiting anti-histamine activity, to processes for preparing them, to novel intermediates involved in their preparation, to pharmaceutical compositions containing them and to their use in medicine.

U.S. Pat. No. 2,567,245 discloses a group of pyridyl aliphatic amines with antihistamine activity and specifically discloses 3-(p-bromophenyl)-3-(2-pyridyl)-N,N-dimethylpropylamine and 3-(p-chlorophenyl)-3-(2-pyridyl)-N,N-dimethyl-propyl-amine which are hereinafter referred to by their generic names brompheniramine and chlorpheniramine respectively.

U.S. Pat. No. 2,712,023 discloses a group of pyridyl propenylamines with antihistamine activity, the most outstanding of which is the compound named (E)-1-(4-methylphenyl)-1-(2-pyridyl)-3-pyrrolidinoprop-1-ene and hereinafter referred to by its generic name, triprolidine. Triprolidine has gained widespread clinical acceptance and is one of the most potent antihistamines available.

Triprolidine is known to be metabolized in man to (E)-1-(4-carboxyphenyl)-1-(2-pyridyl)-3-pyrrolidino-prop-1-ene which has little or no antihistamine activity.

The antihistamines now in use, including diphenylhydramine, the pheniramines, pyrilamine, promethazine and triprolidine have one potential disadvantage in common; they all cause sedation or drowsiness in some patients.

A novel group of compounds having antihistamine activity has now been discovered.

Accordingly this invention provides a compound of the formula (I):

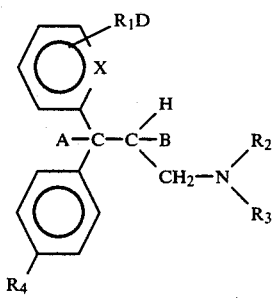

or a salt, ester, or amide or other protected form thereof; wherein
$R_1$ is $C_{1-7}$ bivalent aliphatic hydrocarbon group or a single bond;
$R_2$ and $R_3$ are the same or different and are each hydrogen, $C_{1-4}$ alkyl or taken together with the nitrogen comprise a nitrogen-containing heterocyclic ring having four to six ring members;
$R_4$ is hydrogen, halogen, hydroxy, cyano, $C_{1-4}$ acyloxy, $C_{1-4}$ alkoxy or $C_{1-4}$ alkyl optionally substituted by one to three halogen atoms;
X is —N= or —CH=;
A and B each represent hydrogen atoms or —CA—CB— represents —C=C—; and
D is an acidic group other than a mono-carboxylic acid group.

In a preferred aspect D is an acidic group such that the acid H—D has a pKa of $\leq 7$. In one particularly preferred aspect, the acid group D is a hydroxamic acid group. In another particularly preferred aspect, D is an acidic group, (D') other than a carboxylic acid group, of comparable or greater acid strength than a carboxylic acid group in a similar chemical situation.

Of the compounds of formula (I) those of formula (II) are preferred.

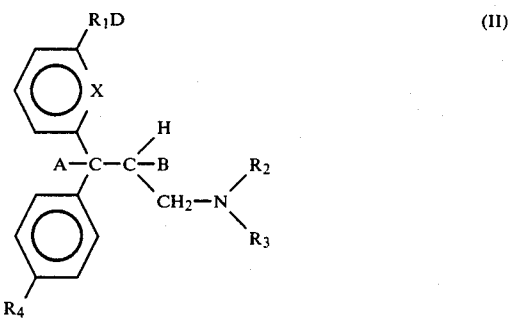

or a salt, ester or amide or other protected form thereof; wherein $R_1$ to $R_4$, X, A, B and D are as defined in relation to formula (I).

$R_1$ may be a straight or branched chain, saturated or unsaturated hydrocarbon group or a single bond. Suitably $R_1$ is a straight chain hydrocarbon group or a single bond. Suitably $R_1$ contains at the most one double or triple bond. Preferably $R_1$ is a group $(CH_2)_n$ wherein n is an integer 0 to 7, or a group $(CH_2)_a$ CH=CH$(CH_2)_b$ where a and b are independently 0 to 5 and the sum of a and b does not exceed 5, or $R_1$ is a group —CH(CH$_3$)(CH$_2$)$_m$ wherein m is 0 or 1, or a group —C(CH$_3$)$_2$—.

Suitable n is 0 to 3 and preferably n is 2. Suitably the sum of a and b does not exceed 2 and preferably a and b are both 0.

Suitably D is a sulphonic or phosphonic acid, or an amide thereof such as a sulphonamide; hydroxamic acid or an optionally substituted heterocyclic ring that contains an acidic hydrogen atom. In one preferred embodiment D is a heterocyclic ring that contains an acidic hydrogen atom, for example tetrazole. In a second preferred embodiment the group D is hydroxamic acid, and, in a third preferred embodiment, the group D is a sulphonic acid group or an acidic amide or ester thereof.

Suitably $R_2$ and $R_3$ are the same or different and each is methyl or ethyl or taken together with the nitrogen atom to which they are attached form a four to six membered heterocyclic ring, preferably a saturated heterocyclic ring such as pyrrolidine, piperidine or morpholine. NR$_2$R$_3$ is preferably a pyrrolidino group or a dimethylamino group.

Suitably $R_4$ is hydrogen, halogen, $C_{1-4}$ alkyl, $C_{1-4}$ alkoxy or trifluoromethyl. Most suitably $R_4$ is hydrogen, methyl, ethyl, trifluoromethyl, methoxy, bromo, chloro or fluoro. Preferably $R_4$ is methyl, trifluoromethyl, methoxy, bromo or chloro. Most preferably $R_4$ is methyl.

Preferably X is —N=.

A preferred group of compounds of the formula (I) is that of the formula (III):

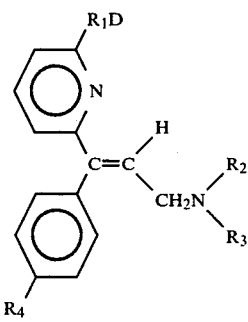

(III)

or a salt, ester or amide or other protected form thereof; wherein $R_1$ to $R_4$ and D are as hereinbefore defined. Of the compounds of the formula (III), those wherein $R_1$ is a single bond (i.e. n=O), CH=CH or $CH_2CH_2$, $NR_2R_3$ is pyrrolidino and $R_4$ is methyl or trifluoromethyl are particularly preferred.

A further preferred group of compounds of the formula (I) is that of the formula (IV)

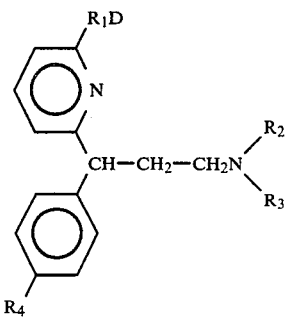

(IV)

or a salt, ester or amide or other protected form thereof; wherein $R_1$ to $R_4$ are as hereinbefore defined. Of the compounds of the formula (V), those wherein $R_1$ is a single bond, CH=CH or $CH_2CH_2$, $NR_2R_3$ is dimethylamino and $R_4$ is chlorine or bromine are particularly preferred.

Suitable protecting groups for the acidic group D are those well known to those skilled in the art (see for example, Protecting Groups in Organic Chemistry, ed. J. F. W. Mc Omie, Plenum Press, London, 1973) and may include alkyl, aralkyl, aralkyl, trialkylsilyl and groups such as alkoxycarbonylethyl or cyanoethyl which may be readily removed by a retro-Michael reaction.

Amides of the compounds of the formula (I) included within the scope of the invention are amides conventionally formed from sulphonic or phosphonic acids. Amides formed from ammonia, primary amines or amino acids, such as glycine, are particularly suitable.

Solvates of the compounds of the formula (I) are also included within the scope of the present invention. Preferred solvates include hydrates and $C_{1-4}$ alkanolates.

When the compounds of formula (I) contain a double bond in the side chain terminating in the group $NR_2R_3$, for example the compounds of formula (III), they exist in either the cis or trans isomeric form(s) (in relation to the X-containing ring). The compounds of the formula (III) have been drawn in the trans configuration and these are the isomers which primarily have useful antihistamine activity. The compounds in the cis configuration are primarily useful as intermediates in preparing the trans isomers.

The present invention also provides mixtures of the isomers. When $R_1$ in the substituent $R_1D$ contains a double bond, further isomers of the compounds of the formula (I) exist, and both isomers and the isomeric mixture of these compounds are included within the scope of the present invention.

Esters and amides of the compounds of the formula (I) may have antihistamine activity in their own right and may also be useful intermediates in the preparation of the acids of the formula (I). Suitable esters include conventional ester groups known to be useful for protecting sulphonic or phosphonic acid groups such as $C_{1-6}$ alkyl esters wherein the alkyl group is straight or branched chain and is optionally substituted by halogen. Alkyl esters ($C_{1-4}$) are particularly preferred.

Salts of the compounds of formula (I) may be either acid addition salts or salts formed with the acid group. Acid addition salts are preferred but salts formed from the acid group may be particularly useful in preparing the corresponding acid. Pharmaceutically acceptable salts are preferred.

When used in medicine, the salts of the compound of formula (I) should be both pharmacologically and pharmaceutically acceptable, but non pharmaceutically acceptable salts may conveniently be used to prepare the free active compound or pharmaceutically acceptable salts thereof and are not excluded from the scope of this invention. Such pharmacologically and pharmaceutically acceptable acid addition salts include, but are not limited to, those prepared from the following acids: hydrochloric, sulphuric, nitric, phosphoric, maleic, salicyclic, toluene-p-sulphonic, tartaric, citric, methanesulphonic, formic, malonic, isothionic, succinic, naphthalene-2-sulphonic and benzenesulphonic. Also, pharmaceutically acceptable salts can be prepared as alkaline metal or alkaline earth salts, uch as sodium, potassium or calcium salts of the carboxylic acid group.

Preferred compounds of the formula (I) include:
(E)-3-[6-(3-pyrrolidino-1-(4-tolyl)prop-1E-enyl)-2-pyridyl]acrylohydroxamic acid;
6-[3-pyrrolidino-1-(4-tolyl)prop-1-enyl]pyridine-2-sulphonic acid;
5-(E)-(6-(3-pyrrolidino-1-(4-tolyl)prop-1E-enyl)-2-pyridylvinyl)-1H-tetrazole;
(E)-3-(1-phenyl-3-pyrrolidinoprop-1-enyl)-benzenesulphonic acid, and
3-(1-phenyl-3-pyrrolidinopropyl)benzenesulphonic acid or salts or solvents thereof.

The present invention also provides a method for preparing compounds of the formula (I), which method comprises:
(a) The reaction of a compound of the formula (V)

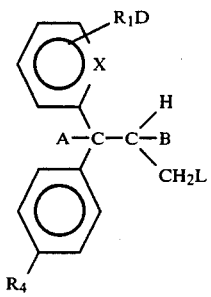 (V)

or a protected form thereof with an amine $HNR_2R_3$ wherein X, A, B, D and $R_1$ to $R_4$ are as hereinbefore defined and L is a leaving group;

(b) The conversion of a compound of the formula (I) wherein the substituent on the X-containing ring is $R_1CO_2H$ to a compound of the formula (I) wherein D is an acid group as hereinbefore defined.

(c) When it is required to prepare a compound of the formula (I) wherein CA-CB represents a double bond:

(i) The reaction of a suitably protected derivative of a compound of the formula (VI):

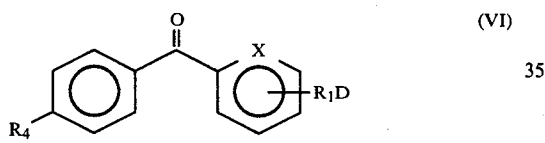 (VI)

with a Wittig reagent suitable for attaching the side chain $=CHCH_2NR_2R_3$ wherein, X and $R_1$ to $R_4$ are as hereinbefore defined, followed by deprotection of the acid group if desired;

(ii) The elimination of $R_5OH$ from a compound of the formula (VII):

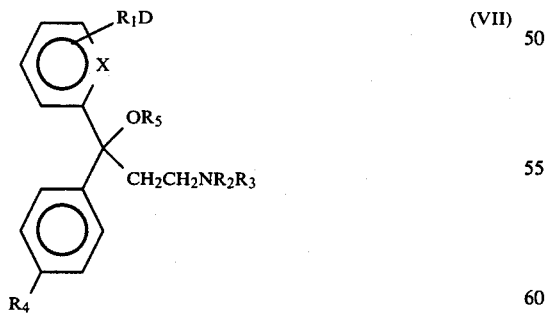 (VII)

or a protected form thereof, wherein X, $R_1$ to $R_4$ and D are as hereinbefore defined and $R_7$ is hydrogen or $C_{1-4}$ acyl;

(iii) The reaction of a compound of the formula (VIII):

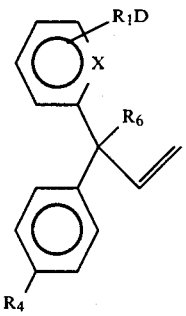 (VIII)

with an amine $HNR_2R_3$, wherein $R_1$ to $R_4$ and D are as hereinbefore defined and $R_6$ is a $C_{1-4}$ acyloxy group;

(d) and thereafter, optionally converting one compound of the formula (I) to another compound of the formula (I) by methods well known to those skilled in the art, for example the isomerisation of a compound of the formula (IX)

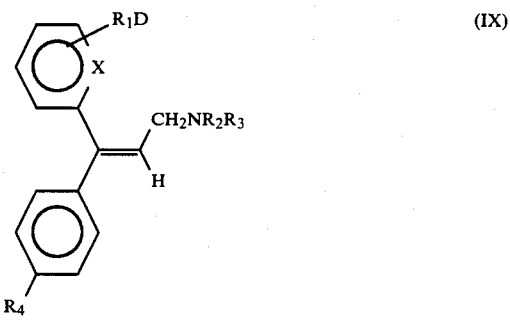 (IX)

when CA—CB is a double bond, the reduction of one or more double bonds or removal of a protecting group from a protected form of the compound of the formula (I).

It will be apparent to those skilled in the art that certain methods of preparation will be more suitable than others for preparing compounds of the formula (I) depending upon the nature of the acid group D.

(a) Suitable leaving groups L in the compounds of the formula (V) are those as defined by J. March, *Advanced Organic Chemistry*, 2nd ed., pages 683 and 895, McGraw Hill, New York, 1977, e.g. —Br, —Cl, toluene sulphonate, methane sulphonate, acyloxy (such as acetate), etc.

This reaction will normally be carried out in a solvent suitable for carrying out such displacement reactions, for example a polar solvent, such as a $C_{1-4}$ alkanol or a polar aprotic solvent such as DMSO, at a temperature between 0° and 180° C.

The compounds of the formula (V) may be prepared by the reaction of the corresponding compound where L is a hydroxy group with an acid or a suitable reactive acid derivative. Suitable reactants include hydrogen halides, halogenated phosphorus compounds such as phosphorus pentachloride or phosphorus oxychloride, a suitable sulphonyl chloride (such as methane sulphonyl chloride or p-toluene sulphonyl chloride) or an acid anhydride, such as acetic anhydride. The reaction will conveniently be carried out in a suitable solvent under conditions well known to those skilled in the art, for example a non-protic solvent such as an ether or a halogenated hydrocarbon, in the present of a base such as a tertiary amine (for example triethylamine) at a non-extreme temperature, for example between 0° and 100° C. and conveniently at room temperature. When a tertiary amine is used as a base, an excess of this may be used as the solvent. When D is a sulphonic or phosphonic and, this is preferably converted to an ester thereof before the compounds of the formula (V) are prepared. This acts as a protecting group and can be removed after the reaction is complete if desired.

The hydroxy compounds may be prepared by the reaction of a compound of formula (VI) with an appropriate Wittig reagent containing a protected hydroxy group for example $(R_7)_3P=CHCH_2O$ wherein $R_7$ is a $C_{1-4}$ alkyl or phenyl group, which is liberated by the action of strong base on the corresponding phosphonium salt $Hal^-(R_7)_3P^+CH_2CH_2O-$ where Hal is chlorine or bromine.

The compounds of the formula (V) may also be prepared by the rearrangement of a compound of the formula (VIII). This rearrangement is suitably carried out in the presence of a catalyst, for example a suitable solubilised palladium catalyst, such as bis-(benzonitrile)-palladium (II) dichloride or bis-(acetonitrile)palladium (II) dichloride, in a suitable solvent, in a suitable polar aprotic solvent, such as acetonitrile, at a non-extreme temperature, for example between 20° and 120° C., most suitably between 40° and 90° C.

(b) The preparation of a compound of the formula (I) from the corresponding compound where the substituent on the X containing ring is $R_1CO_2H$ will be carried out under conventional conditions well known to those skilled in the art. The carboxylic acid group is conveniently converted into an activated derivative, for example an acid anhydride or acid halide, in the first step of this reaction. This will be done under standard condition ie. in an aprotic solvent, such as a halogenated hydrocarbon, an ether or a dipolar aprotic solvent at a non-extreme temperature of between −50° and 100° C., preferably at room temperature. The activated acid derivative is then reacted with a substance that will give a compound of the formula (I) or an intermediate for this. A man skilled in the art will know which substances need to be used to give the different acid groups D. For example, the compound of the formula (I) wherein D is tetrazole is prepared by the following reaction scheme.

Hal=halogen, e.g. chlorine

Other heterocyclic acid groups may be prepared in a similar manner. Hydroxamic acid may be prepared as follows.

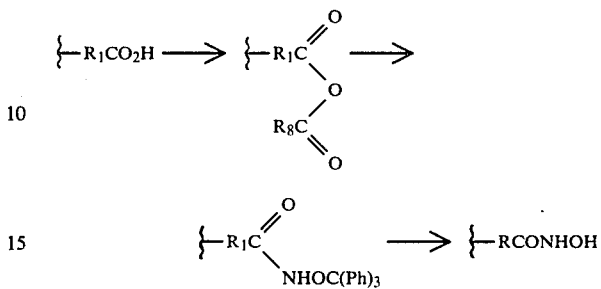

The compounds of the formula (I) wherein the substituent on the X-containing ring is $R_1CO_2H$ are prepared as described in U.K. Patent Application 8302971.

(c(i)) This reaction is a conventional Wittig reaction and, as such, is analogous to those described in *Organic Reactions*, 14, 270–490 (1965) and *Pure and Applied Chemistry*, 9, 245–254 (1964). The reaction is suitably carried out in an anhydrous solvent inert under the reaction conditions utilised, for example toluene, benzene, tetrahydrofuran, dioxan, glycol ethers and $C_{1-6}$ alkyl ethers such as ethyl ether, at a temperature between −80° C. and 100° C. The Wittig reagent will normally be prepared by treatment of a phosphonium salt with a strong base, for example a $C_{1-4}$ alkyl or aryl lithium compound such as butyl lithium, or a metal hydride, such as sodium hydride in a suitable inert solvent, such a those specified above.

The Wittig reagent is conveniently a compound of the formula $(R_7)_3P=CHCH_2NR_2R_3$ which can be liberated from its corresponding phosphonium salt $(R_7)_3P^+CH_2CH_2NR_2R_3Hal^-$ wherein Hal, $R_2$, $R_3$ and $R_7$ are as hereinbefore defined by reaction with a strong base. The reaction is suitably carried out in an inert solvent such as toluene or tetrahydrofuran at a temperature of between 0° and 50° C. and conveniently at room temperature. Suitably the strong base is an alkyl or aryl lithium compound, such as butyl lithium, or a metal hydride, such as sodium hydride. The use of butyl lithium in toluene at room temperature has been found to be particularly convenient. The phosphonium salts $(R_7)_3P^+CH_2CH_2NR_2R_3Hal^-$ may be prepared by $R_8=C_{1-6}$ alkyl known methods (see, for example, UK Patent No. 1161201).

Compounds of formula (VI) in which $R_1$ is —CH═CH— (trans) may be prepared by reacting a compound of formula (X) with a compound of the formula (XI) wherein $R_4$ and D are as defined above, and Hal is halogen, particularly bromine, and in which the acid group D is protected where appropriate in the presence of a catalyst consisting of palladium acetate and a triarylphosphine and a tertiary amine such as triethylamine or tributylamine at an elevated temperature, for example 120° to 180° C., conveniently 140° to 150°. The reaction may be carried our under pressure to achieve the desired temperature range if desired. Optionally a solvent such as acetonitrile may be used and the reactants may be heated together in a sealed pressure vessel (e.g see R. F. Heck et al., J. Org. Chem., 43, 2947 (1978)).

Compounds of the formula (VI) wherein $R_1$ is a bond, D is a sulphonic acid group and X is nitrogen are advantageously prepared by reacting the corresponding compound of the formula (X) with a thiolating agent such as sodium hydrosulphide, followed by oxidation of the corresponding thiol to the sulphonic acid, for example with hydrogen peroxide.

Compounds of the formula (VI) wherein $R_1$ is a bond, D is a sulphonic acid group and X is —CH═ may be prepared by Friede l-Crafts acylations in a manner analogous to that described by Dart and Holt in *J. Chem. Soc., Perkin Trans. I*, 1974, 1403.

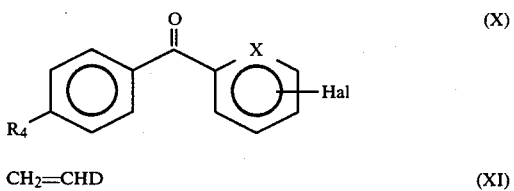
(X)

$CH_2$═CHD (XI)

Compounds of formula (VI) may also be prepared by reacting a compound of formula (XII):

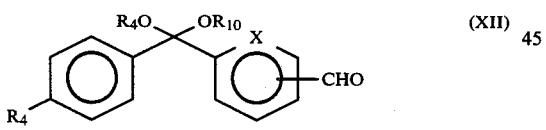
(XII)

wherein $R_9$ and $R_{10}$ may be the same or different and are each $C_{1-4}$ alkyl, or may together form a cyclic ketal containing up to 6 carbon atoms, with malonic acid in the presence of a suitable base such as as pyridine or piperidine, or with a Wittig reagent prepared by treating a phosphonium salt (XIII A) or a phosphonate ester (XIII B) (where D can form an ester group) with a suitable base in an appropriate solvent:

$(R_7)_3P^+(CH_2)_dDHal^-$ (XIII A)

$(R_{11})_2PO(CH_2)_dD$ (XIII B)

wherein Hal, $R_7$ and D are as defined above, $R_{11}$ is $C_{1-4}$ alkoxy and d is 1–6. The ketone (VI) is generated by acidic hydrolysis of the protecting ketal. The double bond in the group $R_1$ may be reduced if desired with hydrogen in presence of a catalyst such as palladium on charcoal.

Compounds of formula (XII) may be prepared from compounds of formula (X) by conversion to a ketal by reaction with a mono or dihydroxy compound in the presence of an acid catalyst followed by reaction with a metal alkyl compound, for example butyllithium, and subsequent treatment with dimethylformamide. The reaction is preferably conducted at low temperature (below −60° C.) in a solvent such as toluene.

In turn compounds of formula (X) can be prepared by treatment of a compound of formula (XIV) with a metal alkyl compound, for example butyllithium, in a suitable solvent such as toluene, followed by reaction with a compound of formula (XV) wherein Hal is halogen such as chlorine or bromine and $R_4$ is as hereinbefore defined.

(XIV)

(XV)

(c(ii)) The elimination of $R_5OH$ from compounds of formula (VII) is conveniently accomplished in the presence of a strong mineral acid, for example concentrated sulphuric acid, at an elevated temperature, for example between 100° and 200° C., suitably 125° to 150° C.

The compounds of formula (VII) may be prepared by the reaction of a compound of the formula (XVI):

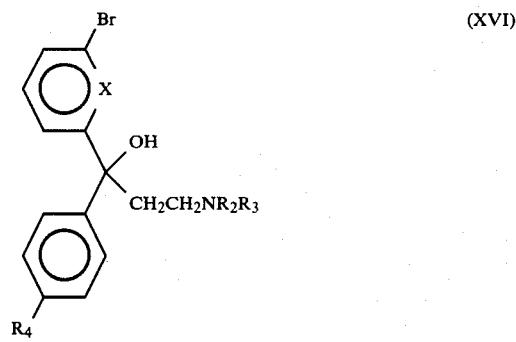
(XVI)

with CH═CHD wherein X and $R^2$ to $R^4$ are as hereinbefore defined and D is an acid group as hereinbefore defined which is protected when appropriate. This reaction is conveniently carried out in the presence of a catalyst consisting of palladium acetate and a triaryl phosphine and in the presence of a tertiary amine, conveniently a water soluble tertiary amine such as N-ethylmorpholine. The compound of the formula (XVI) is conveniently prepared from the reaction of a compound of formula (XIV) with a metal alkyl compound such as butyl lithium followed by reaction with a compound of the formula (XVII):

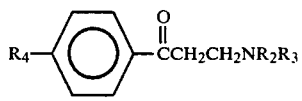

(XVII)

This reaction is suitably carried out at low temperature, for example between −90° and −30° C., conveniently between −70° and −40° C., in an inert solvent, for example toluene, and in an inert atmosphere.

(c(iii)) The reaction of a compound of formula (VIII) with an amine $HNR_2R_3$ is suitably carried out in the presence of a palladium catalyst. The reaction is conveniently carried out in a polar aprotic solvent, such as acetonitrile, at an elevated temperature, for example between 20° and 100° C., suitably between 30° and 80° C. and conveniently between 50° and 70° C. This reaction is conveniently carried out on a protected derivative of a compound of the formula (VIII).

The compounds of formula (VIII) may conveniently be prepared by the acylation of the corresponding compound wherein $R_6$ is a hydroxy group. The reaction is suitably carried out by the use of the appropriate acyl anhydride in the presence of base, for example triethylamine. The use of 4-N,N-dimethylaminopyridine as a catalyst has been found to facilitate this reaction. The preparation of the hydroxy compounds is suitably carried out by the reaction of a compound of the formula (VI) with a Grignard reagent $CH_2=CHMgHal$ wherein Hal is a suitable halogen atom such as bromine. This reaction is carried out under conditions conveniently used for Grignard reactions, for example in an inert anhydrous solvent such as tetrahydrofuran and can advantageously be carried out in the presence of zinc chloride thereby generating divinyl zinc which reacts with the compound of the formula (VI) in situ.

(e) The isomerization of a compound of the formula (IX) is suitably carried out in the presence of in excess of one molar equivalent of a strong acid, suitably a strong mineral acid, for example sulphuric acid, at an elevated temperature, for example between 50° and 160° C., conveniently between 125° and 150° C.

The compounds of the formula (IX) may be prepared as by-products in some of the reaction methods for the preparation of compounds of the formula (I) and may be obtained from the reaction mixture by conventional separation techniques, for example by chromatography or by techniques that rely on solubility differences between the two isomers in a suitable solvent, for example, it has been found that when it is required to prepare a compound of the formula (III) as the free acid, it is often convenient to prepare the corresponding ester, where appropriate, and then saponify this, for example with an alkali metal hydroxide, such as sodium hydroxide, in a $C_{1-4}$ alkanol, such as ethanol, to give the acid.

The reduction of one or two double bonds, i.e. the reduction of the double bond terminating in the group $NR_2R_3$ or the reduction of its double bond in the carboxy side chain may conveniently be carried out by hydrogen in the presence of a transition metal catalyst, for example platinum or charcoal. The preparation of esters or amides from the corresponding carboxylic acid, and vice versa, may similarly be carried out by methods well known to those skilled in the art.

Those intermediates of the formulae (V) to (XVII) that are novel form an important further aspect of the present invention. The intermediates of the formulae (V) to (IX) are preferred intermediates.

The compounds of this invention may be used for the same indications as triprolidine, namely to relieve symptoms of nasal stuffiness due to colds and vasomotor rhinitis and for the symptomatic control of allergic conditions including nasal allergy, perennial rhinitis, urticaria, angioneurotic oedema, allergic conjunctivitis, food allergy, drug and serum reactions, insect bites and stings and desensitizing reactions. The compound may also be used in conditions responsive to its antipruritic activity including allergic dermatoses, neurodermatitis, anogenital pruritus, and pruritus of non-specific origin such as eczema, and of specific cause such as chickenpox, photosensitivity and sunburn. The present invention therefore provides a method for the symptomatic treatment of allergic conditions by the administration of an effective amount of a compound of the formula (I). The present invention also provides a method for the antagonism of endogenously released histamine by the administration of an effective amount of a compound of the formula (I). Some of the compounds of the present invention have been found to be substantially free from sedative effects and to have little or no anticholinergic effects.

The amount of active compound required for use in the above conditions will vary with the compound chosen, the route of administration and the condition and mammal undergoing treatment, and is ultimately at the discretion of the physician. A suitable oral dose of the active compound for a mammal is in the range of from 0.003 to 1.0 mg per kilogram body weight per day; preferably from 0.04 to 0.24 mg/kg. For example a typical dose for a human recipient of compound (A) (see example 1 hereafter) is 0.12 mg/kg body weight per day.

The desired daily dose is preferably presented as from one to six sub-doses administered at appropriate intervals throughout the day as needed. Where three sub-doses of compounds of formula (I) are employed, each will preferably lie in the range of from 0.014 to 0.08 mg/kg body weight; for example, a typical sub-dose of such a compound for a human recipient is between 1 and 20 mg, for example 4 or 8 mg.

Whilst it is possible for a compound of the formula (I) to be administered alone as the raw chemical, it is preferable to present the compound of formula (I) as a pharmaceutical formulation. Thus, the present invention also provides pharmaceutical formulations, both for veterinary and for human medical use, which comprise a compound of the formula (I) together with one or more pharmaceutically acceptable carriers thereof and optionally any other therapeutic ingredients. For example, the active compound may be formulated with a sympathomimetic agent such as the decongestant pseudoephedrine, an antitussive such as codeine, an analgesic, an antiinflammatory, an antipyretic, or an expectorant. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into associatiohn with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquor or non-aqueous liquid such as a syrup, and elixir, an emulsion or a draught.

A tablet may be made by compression or moulding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Moulded tablets comprised of a mixture of the powdered active compound with any suitable carrier may be made by moulding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol, for example glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except that the pH and isotonic factors are adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

The present invention also provides the first use of the compounds of the formula (I) in medicine.

The following Examples are provided by the way of illustration of the present invention and should in no way be construed as a limitation thereof. All temperatures indicated are in degrees Celsius.

EXAMPLE 1

5-(E-6-[3-Pyrrolidino-1-(4-tolyl)prop-1E-enyl]-2-pyridylvinyl)-1H-tetrazole.

A solution of isobutyl chloroformate (0.7 g.) in dry dichloromethane (6 ml) was added to a stirred solution of (E)-3-(6-[3-pyrrolidino-1-(4-tolyl)prop-1E-enyl]-2-pyridyl)acrylic acid (1.85 g.) (B. P. Appn. No 8302971, Ex1). in dichloromethane (30 ml) at $-25°$. After two minutes, N-methylmorpholine (1 g.) was added, followed at once by $\beta$-alanine methyl ester hydrochloride (0.2 g.) in dichloromethane (15 ml). After stirring at 0° for 2 hrs saturated sodium bicarbonate solution (15 ml) was added and stirring continued for 0.5 hr. The organic phase, was separated, washed with water, dried and evaporated to dryness. The resulting gum (2.5 g) was dissolved in methanol and treated with a slight excess of hydrochloric acid. Addition of ether precipitated the hydrochloride which formed colourless prisms from methyl acetate, m.p. 184–6 (1.8 g.).

A stirred solution of this salt (1.8 g.) in dichloromethane (20 ml) containing pyridine (0.31 ml) was treated with phosgene (0.42 g.) in dichloromethane (5 ml). After 2.5 hrs excess phosgene was removed by passing a stream of nitrogen and azidotrimethylsilane (0.52 ml) was added. Next day the solvents were evaporated and the residual oil was partially purified by column chromatography on silica using ethanol as eluant. The major fraction (1.35 g.) was deprotected by treatment in chloroform solution with 3 equivalents of 1,5-Diazabicyclo (4.3.0) non-5-ene for ten days at room temperature. The solution was extracted with dilute acetic acid, washed with water, dried and evaporated. Trituration of the residual oil with ether gave a solid which was purified by crystallisation from aqueous methanol. The title compound formed. Cream coloured prisms, m.p. 128–130.

EXAMPLE 2

(E)-3-(1-phenyl-3-pyrrolidinoprop-1-enyl)-benzenesulphonic Acid

Butyllithium (7 ml, 1.6M in hexane) was added to a stirred ice-cooled suspension of triphenyl-2-pyrrolidinoethylphosphonium bromide (4.26 g.) in dry tetrahydrofuran (25 ml).

After 0.5 hr. the solid sodium salt of 3-benzoylbenzene-sulphonic acid (1) (2.75 g.) was added, and the mixture was stirred at room temperature for four hours. Ether (50 ml) and water (50 ml) were added. The aqueous phase was separated, washed with ether, and neutralised with dilute hydrochloric acid. A gummy material separated (1 g); extraction of the water layer with chloroform afforded, after evaporation, a further 2.5 g of the same mixture. Purification of these products was achieved by flash chromatography on silica gel using chloroform methanol mixtures as eluant. The E-isomer formed a white amorphous powder with the expected analytical and spectral properties.

mp 223°–225° C.;

T.l.C. (silica, CHCl$_3$:MeOH (1:1)) single spot Rf=0.35; Analysis: Calculated for C$_{19}$H$_{21}$No$_3$S. 0.2H$_2$O; C, 65.77; H, 6.22; N, 4.03; S, 9.22; H$_2$O 1.03 Found; C, 65.71; H, 6.10; N, 3.92; S, 9.22: Loss at 110° C., 0.98; Ref. 1. E. C. Dart and G. Holt, J. C. S. Perkin I, 1974, 1403.

EXAMPLE 3

3-(1-phenyl-3-pyrrolidinopropyl)benzenesulphonic acid

A solution of 3-(1-phenyl-3-pyrrolidinoprop-1-enyl benzenesulphonic acid (0.65 g.) in water (50 ml) containing 10% Pd-C catalyst (0.05 g.) was stirred under hydrogen at room temperature and pressure until the theoretical equivalent of hydrogen has been absorbed (55 ml, ca. 2 hrs.). Filtration and evaporation gave a gum, which crystallised on trituration with isopropanol. After drying at 100° in vacuo, an amorphous powder with the expected analytical and spectral properties was obtained.

EXAMPLE 4

6-[3-pyrrolidino-1-(4-tolyl)prop-1-enyl]pyridine-2-sulphonic acid

To a stirred solution of sodium hydrosulphide hydrate (22.0 g) in ethylene glycol (100 ml) at 100° C. was added 2-bromo-6-(4-toluoyl)pyridine (27.6 g) in portions. The mixture was then heated at 110° C. for 3 hours, allowed to cool and then poured into water (600 ml). The yellow precipitate of the by-product 6-(4-methylbenzyl)pyridine-2-thiol was filtered off and the filtrate was acidified by the addition of glacial acetic acid (10 ml). The resultant orange solid was then filtered off and well washed with water and dried. This crude solid (19.4 g) was crystallised from a mixture of benzene (500 ml) and methanol (175 ml) to give 6-(4-toluoyl)pyridine-2-thiol (10.0 g) as orange needles. M.p. 179°–181°.

This thiol (9.16 g) was dissolved in a solution of barium hydroxide octahydrate (12.62 g) in water (250 ml) and the solution filtered. To the stirred and ice-cooled solution was then added dropwise 30% aqueous hydrogen peroxide (14.0 ml). After allowing to warm to room-temperature the mixture was heated on the steam bath for one hour with stirring. The resultant solution was filtered hot and then allowed to cool whereupon the barium salt of the sulphonic acid crystallised from solution. To the suspension of the barium salt was added with stirring 1.0N aqueous sulphuric acid (40 ml) and the resultant mixture heated on the steam bath for 15 minutes and then allowed to cool. The precipitate of barium sulphate was filtered off and the filtrate concentration to dryness in vacuo and the residue treated with ethanol and reconcentrated to dryness. Trituration with ethanol, filtration and washing with acetone gave 6-(4-toluoyl)pyridine-2-sulphonic acid (8.93 g) as a yellow solid. M.p. >300°.

To a suspension of this suphonic acid (5.54 g) in water (10 ml) was added 1.0N aqueous sodium hydroxide (20 ml). The resultant solution was then concentrated to dryness in vacuo and the residue dissolved in ethanol and reconcentrated to dryness and this process repeated to give a pale yellow solid which was triturated with ether, filtered, and washed with ether and then dried in vacuo at 100°.

To a stirred suspension of triphenyl-2-pyrrolidinoethyl phosphonium bromide (4.40 g) in tetrahydrofuran (25 ml), cooled in ice, was added, under nitrogen, butyl lithium (6.25 ml, 1.60M in hexane). After one hour the sodium salt of the sulphonic acid (2.99 g) was added portionwise finally washing in with tetrahydrofuran (10 ml). The mixture was stirred at room-temperature for 1.5 hours and then heated at 60° C. for one hour and then cooled. Water (40 ml) was then added and the resultant solution extracted with ether (2×40 ml) and the aqueous phase then neutralized by the addition of 1.0N aqueous hydrochloric acid (10.0 ml). The solution was then extracted with chloroform (2×30 ml) and the combined extracts were dried and concentrated in vacuo to give a foam which was triturated with ether to give an amorphous solid (3.60 g). The two main components of this product were then separated by dry column chromatography on silica-gel. Elution with acetone/methanol mixture gave initially the major component, which crystallised on treatment with acetone and was obtained as fine white crystals (1.46 g), m.p. 216°–217° (decomp) TLC (silica-gel, acetone/methanol 20%) Rf 0.35, and was shown by NMR (dmso-d$_6$) to be the Z-isomer (=CH—, 6.21 δ, t, J=7.8 Hz). Further elution gave the minor component which also crystallised from acetone and was then crystallised from water to give white crystals (0.080 g), m.p. 252°–253° C. (decomp.) TLC (as above, Rf 0.12), and was shown by NMR (dmso-d$_6$) to be the E-isomer (=CH—, 7.04 δ, t, J=7.3 Hz).

EXAMPLE 5: ANTIHISTAMINIC ACTIVITY

A.Invitro antihistaminic activity: The longitudinal muscle was isolated from the intact ileum of guinea-pigs (Harley, male 250–400 g) and placed in an organ bath under 300 mg tension. After one hour of equilibration, cumulative concentration-response curves (Van Rossum, J. M., Arch. Int. Pharmacodyn. Ther. 143 299–330, 1963) to histamine wee obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., Br. J. Pharmacol: 14, 48–58, 1959). Regression of Log (dr-1) on Log/B/, where dr is an equiactive response in the presence and absence of antagonist and /B/ is the molar concentration of antagonist, allowed an estimate of pA$_2$, i.e. the negative log of the concentration of antagonist which shifts the control histamine concentration-response curve 2X to the right.

The antihistaminic activities of compounds of the present invention are detailed in table A below.

TABLE A

| Compound of Example No. | pA$_2$ |
|---|---|
| 1 | 8.7 |
| 2 | 7.1 |
| 3 | 7.3 |

EXAMPLE 6: FORMULATIONS

| (A)-Injection | |
|---|---|
| Ingredient | Amount per ampoule |
| Compound of formula (I) | 1.0 mg |
| Water for Injections q.s | 1.0 mL |

The finely ground active compound was dissolved in the water for Injections. The solution was filtered and sterilized by autoclaving.

| (B)-Suppository | |
|---|---|
| Ingredient | Amount per Suppository |
| Compound for Formula (I) | 1.0 mg |
| Cocoa Butter, | 2.0 |

-continued

| (B)-Suppository | |
|---|---|
| Ingredient | Amount per Suppository |
| or Wecobee TM Base q.s. | |

Wecobee is a trademark and is a hydrogenated fatty carboxylic acid.

The finely ground active compound was mixed with the melted suppository base (either Cocoa Butter or Wecobee TM base), poured into moulds and allowed to cool to afford the desired suppositories.

| (C)-Syrup | |
|---|---|
| Ingredient | Amount Per 5 mL |
| Compound of Formula (I) | 1.0 mg |
| Ethanol | 0.3 mg |
| Sucrose | 2.0 mg |
| Methylparaben | 0.5 mg |
| Sodium Benzoate | 0.5 mg |
| Cherry flavour | q.s |
| Colouring | q.s. |
| Water | q.s.to 5.0 mL |

Ethanol, sucrose, sodium benzoate, methylparaben, and flavouring were combined in 70% of the total batch quantity of water. Colouring and the active compound were dissolved in the remaining water, then the two solutions were mixed and clarified by filtration.

| (D)-Tablet | |
|---|---|
| Ingredient | Amount per Tablet |
| Compound of Formula (I) | 1.0 mg |
| Lactose | 110.0 mg |
| Corn Starch, Pregelantinized | 2.5 mg |
| Potato Starch | 12.0 mg |
| Magnesium stearate | 0.5 mg |

The active compound was finely ground and intimately mixed with the powdered excipients lactose, corn starch, potato starch and magnesium stearate. The formulation was then compressed to afford a tablet weighing 126 mg.

| (E)-Capsule | |
|---|---|
| Ingredient | Amount per Capsule |
| Compound of Formula (I) | 1.0 mg |
| Lactose | 440.0 mg |
| Magnesium Stearate | 5.0 |

The finely ground active compound was mixed with the powdered excipients lactose, corn starch and stearic acid and packed into gelatin capsules.

| (F)-Tablet | |
|---|---|
| Ingredient | Amount per Tablet |
| Compound of Formula (I) | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet was prepared from the above formulation by the method previously described in Example 6(D).

| (G)-Syrup | |
|---|---|
| Ingredient | Amount per 5 mL |
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavour | q.s. |
| Colour | q.s. |
| Glycerol | 500 mg |
| Sucrose | 2000 mg |
| Purified Water q.s to | 5.0 mg |

A syrup containing other active ingredients in addition to a coupound of formula (I) was prepared from the above ingredients by an analogous method to that described for Example 6(C) above.

| (H)-Nasal Spray | |
|---|---|
| Ingredient | Amount per 100.0 mL |
| Compound of Formula (I) | 1 g |
| Sodium Chloride | 0.8 g |
| Preservative | 0.5 g |
| Purified Water q.s. | 100.0 mL |

The preservative was dissolved in warm purified water and after cooling to 25°-30° C. the sodium chloride and the compound of formula (I) were added. The pH was then adjusted to 5.5-6.5 and purified water was added to bring the final volume to 100.0 mL.

| (I)-Ophthalmic Solution | |
|---|---|
| Ingredient | Amount per 100.0 mL |
| Compound of Formula (I) | 0.1 g |
| Sodium Chloride | 0.8 g |
| Preservative | 0.5 g |
| Water for Injection q.s. | 100.0 mL |

This formulation was prepared in a similar way to the nasal spray.

| (J)-Topical Cream | |
|---|---|
| Ingredient | Amount per 100.0 mL |
| Compound of Formula (I) | 0.1 g |
| Emulsifying Wax, N.F. | 15.0 g |
| Mineral Oil | 5.0 g |

EXAMPLE 7

(E)-3-[6-[3-Pyrrolidino-1-(4-tolyl)prop-1E-enyl]-2-pyridyl]acrylohydroxamic acid Isobutyl chloroformate (0.72 g) in dichloromethane (3 cm$^3$) was added at $-25°$ C. under nitrogen to a solution of (E)-3-[6-[3-pyrrolidino-1-(4-tolyl)prop-1E-enyl]-2-pyridyl]acrylic acid (1.74 g) in dichloromethane (25 cm$^3$) containing N-methylpyrrolidine (0.5 g). After two minutes trityloxyamine (1.38 g) in dichloromethane (15 cm$^3$) was added and the resulting mixture was stirred at 0° C. for three hours. The solution was then washed with saturated sodium bicarbonate solution followed by brine, dried and was then evaporated down to give an amorphous solid (3 g). The solid was dissolved in benzene (30 cm$^3$) and dry hydrogen chloride gas was passed through the solution. After ten minutes the solvent was decanted and the residue was taken up in water (50 cm³), washed with ether and neutralised to pH 8 with sodium hydroxide. The precipitated gum was extracted with hot water (50 cm³) and the insoluble residue was taken up in hot isopropanol (ca 30 cm³). The isopropanol solution deposited crystals (0.1 g) mp 193°–5° C. Evaporation of the mother liquors and addition of ethyl acetate gave additional crops totalling 0.4 g. The crystalline material was recrystallised twice from SVM to give the title compound as yellow prisms mp 199° C. (decomp.).

We claim:

1. 5-(E-6-[3-Pyrrolidino-1-(4-tolyl)prop-1E-enyl]-2-pyridylvinyl)-1H-tetrazole.

2. A pharmaceutically acceptable salt of 5-(E-6-[3-pyrrolidino-1-(4-tolyl)prop-1E-enyl]-2-pyridylvinyl)-1H-tetrazole.

3. A method of obtaining an antihistaminic effect in a mammal in need thereof comprising administration to said mammal of an effective antihistiminic amount of the compound 5-(E-6-[3-Pyrrolidino-1-(4-tolyl)prop-1E-enyl]-2-pyridylvinyl)-1H-tetrazole or a pharmaceutically acceptable salt thereof.

* * * * *